United States Patent [19]

Kelly

[11] 4,094,884
[45] June 13, 1978

[54] 4α-HYDROXY-6-OXO-2β-ARYLMETHOXY-METHYL-3α-TETRAHYDROPYRANACETIC ACID γ-LACTONES

[75] Inventor: Robert C. Kelly, Kalamazoo, Mich.

[73] Assignee: The Upjohn Company, Kalamazoo, Mich.

[21] Appl. No.: 784,173

[22] Filed: Apr. 4, 1977

Related U.S. Application Data

[62] Division of Ser. No. 676,895, Apr. 14, 1976, Pat. No. 4,032,542.

[51] Int. Cl.$^2$ ............................................ C07D 493/04
[52] U.S. Cl. .................................................. 260/343.6
[58] Field of Search ........................... 260/343.6, 343.5

[56] References Cited

PUBLICATIONS

Chemical Abstracts, vol. 84, 2250cs.

*Primary Examiner*—Alan L. Rotman
*Assistant Examiner*—Jane T. Fan
*Attorney, Agent, or Firm*—Robert A. Armitage

[57] ABSTRACT

The present specification provides novel intermediates and novel processes for the synthesis of Thromboxane $B_2$ (11a-homo-11a-oxa-PGF$_{2\alpha}$), its 15-epimer, and various carboxyl derivatives thereof. In particular, there are disclosed various bicyclic tetrahydrofuran-containing lactones useful in the above processes, and corresponding acyclic lactones.

2 Claims, No Drawings

4α-HYDROXY-6-OXO-2β-ARYLMETHOXY-METHYL-3α-TETRAHYDROPYRANACETIC ACID γ-LACTONES

The present application is a divisional application of Ser. No. 676,895, filed Apr. 14, 1976, now issued as U.S. Pat. No. 4,032,542 on June 28, 1977.

The present invention relates to Thromboxane $B_2$ and associated intermediates and processes, for which the essential material constituting disclosure therefor is incorporated by reference here from Ser. No. 676,890, filed Apr. 14, 1976, now issued as U.S. Pat. No. 4,020,173 on Apr. 26, 1977.

I claim:

1. A thromboxane intermediate of the formula

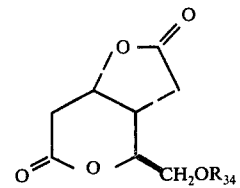

wherein $R_{34}$ is an arylmethyl hydroxy-hydrogen replacing group selected from the group consisting of
 (a) benzyl,
 (b) benzyl substituted by one to five alkyl of one to four carbon atoms, inclusive, chloro, bromo, iodo, fluoro, nitro, phenylalkyl of 7 to 12 carbon atoms, inclusive,
 (c) benzhydryl,
 (d) benzhydryl substituted by one to ten alkyl of one to four carbon atoms, inclusive, chloro, bromo, iodo, fluoro, nitro, phenylalkyl of 7 to 12 carbon atoms, inclusive,
 (e) trityl, and
 (f) trityl substituted by one to 15 alkyl of one to four carbon atoms, inclusive, chloro, bromo, iodo, fluoro, nitro, phenylalkyl of 7 to 12 carbon atoms, inclusive.

2. 4α-Hydroxy-6-oxo-2β-benzyloxymethyl-3α-tetrahydropyranacetic acid γ-lactone, a thromboxane intermediate according to claim 1.

* * * * *